United States Patent [19]

Madaras

[11] Patent Number: 5,691,476
[45] Date of Patent: Nov. 25, 1997

[54] METHOD FOR ULTRASONIC IMAGING AND DEVICE FOR PERFORMING THE METHOD

[75] Inventor: Eric I. Madaras, Yorktown, Va.

[73] Assignee: The United States of America as represented by the Administrator of the National Aeronautics and Space Administration, Washington, D.C.

[21] Appl. No.: 585,087

[22] Filed: Jan. 12, 1996

Related U.S. Application Data

[63] Continuation of Ser. No. 118,466, Sep. 7, 1993, abandoned.
[51] Int. Cl.$^6$ .................................................. G01N 29/04
[52] U.S. Cl. ........................... 73/644; 73/625; 73/629
[58] Field of Search .......................... 73/644, 632, 633, 73/625, 609, 617, 629, 626; 333/140, 141

[56] References Cited

U.S. PATENT DOCUMENTS

| | | | |
|---|---|---|---|
| 4,180,790 | 12/1979 | Thomas | 367/7 |
| 4,217,786 | 8/1980 | Okude et al. | 73/644 |
| 4,267,584 | 5/1981 | McKeighen et al. | 367/11 |
| 4,334,432 | 6/1982 | Gill | 73/602 |
| 4,523,803 | 6/1985 | Arao et al. | 350/358 |
| 4,559,827 | 12/1985 | Kupperman et al. | 73/644 |
| 4,586,381 | 5/1986 | Chamuel | 73/644 |
| 4,684,906 | 8/1987 | Yokoyama | 333/142 |
| 4,894,806 | 1/1990 | Jen et al. | 367/7 |
| 5,159,838 | 11/1992 | Lynnworth | 73/644 |

FOREIGN PATENT DOCUMENTS

| | | | |
|---|---|---|---|
| 376712 | 4/1973 | U.S.S.R. | 73/644 |
| WO87/01269 | 3/1987 | WIPO | 73/644 |

Primary Examiner—Hezron E. Williams
Assistant Examiner—Helen C. Kwok
Attorney, Agent, or Firm—Kimberly A. Chasteen

[57] ABSTRACT

A method for ultrasonic imaging of interior structures and flaws in a test specimen with a smooth or irregular contact surfaces, in which an ultrasonic transducer is coupled acoustically to the contact surface via a plurality of ultrasonic wave guides with equal delay times. The wave guides are thin and bendable, so they adapt to variations in the distance between the transducer and different parts of the contact surface by bending more or less. All parts of the irregular contact surface accordingly receive sound waves that are in phase, even when the contact surface is irregular, so a coherent sound wave is infused in the test specimen. The wave guides can be arranged in the form of an ultrasonic brush, with a flat head for coupling to a flat transducer, and free bristles that can be pressed against the test specimen. By bevelling the bristle ends at a suitable angle, shear mode waves can be infused into the test specimen from a longitudinal mode transducer.

12 Claims, 3 Drawing Sheets

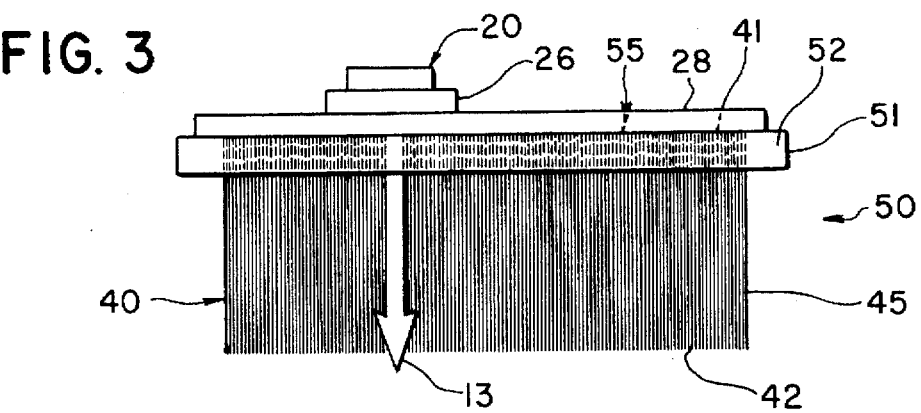
FIG. 3
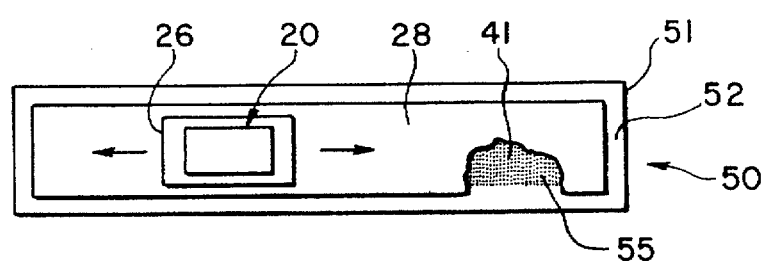
FIG. 4
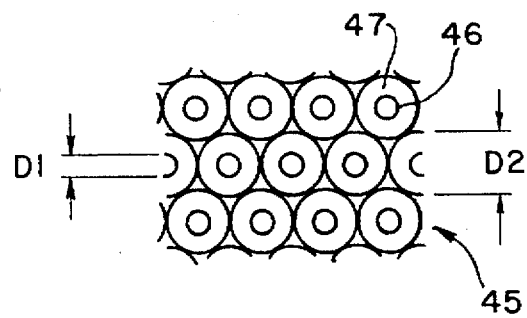
FIG. 5
FIG. 6(a)   FIG. 6(b)   FIG. 7(a)   FIG. 7(b)
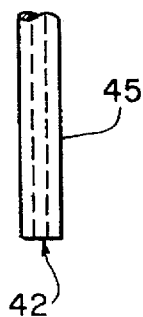 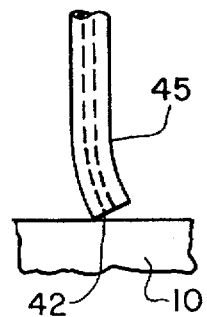 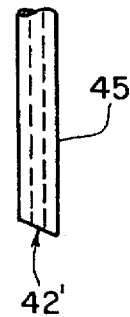 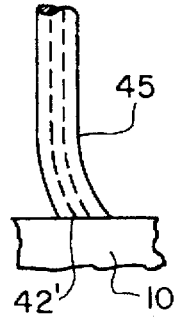

5,691,476

METHOD FOR ULTRASONIC IMAGING AND DEVICE FOR PERFORMING THE METHOD

This is a continuation of application Ser. No. 08/118,466 filed on Sep. 7, 1993 now abandoned.

ORIGIN OF THE INVENTION

The invention described herein by an employee of the U.S. Government and may be used by or for the Government for governmental purposes without the payment of any royalties thereon or therefor.

BACKGROUND OF THE INVENTION

1. Field of the Invention

This invention relates in general to ultrasonic imaging of internal structures and flaws in materials, and specifically to a new method for coupling an ultrasonic transducer to a test specimen with irregular or complex surface geometry and a new device for performing the method. The present invention is applicable to dentistry, evaluation of near surface defects in castings, evaluation of components in aging aircraft, and high resolution acoustic imaging of small components.

2. Description of the Related Art

For most non-destructive evaluation purposes, ultrasound is generated by a flat piezoelectric element that generates a coherent ultrasonic beam, and reflected sound is detected by the same or a similar piezoelectric element. Such a flat ultrasonic transducer can easily couple coherent sound waves into a test specimen with a flat contact surface.

Standard systems can not handle test specimens with irregular surfaces or rapidly varying surface geometry, however, because such surface geometries will cause severe mode conversions, phase distortions, and signal reflections in the coherent ultrasound wave pattern from the transducer. A wet or a dry homogenous couplant layer added between the transducer and the test specimen surface will not help either, because the thickness of the couplant layer varies along the contact surface in such cases, and there is a delay in the ultrasonic wave proportional to the thickness of the couplant layer before it reaches the specimen surface.

For imaging of internal structures or flaws in specimens which are not flat, but otherwise have a uniform or consistent shape, it is known to introduce delay lines compensating for the varying distance between a standard ultrasonic transducer and the surface of the test specimen. The use of matched delay lines solves the problem of injecting ultrasound into a part with a smooth, non-flat contact surface, but it is not suitable for general applicability, and it is not suitable for rapid scanning.

For imaging of internal structures or flaws in specimens with more irregular test surfaces, it is known to generate a tightly focused ultrasound beam, which has such a small and localized area of contact with the surface of the test specimen that the actual contact area can be regarded as smooth. Other methods for generating a small and localized area of ultrasound contact involves generation of ultrasound energy through laser beams or electron beams impinging on the test specimen.

Focusing is limited by physical diffraction limits, and if focused too tightly, the beam may generate surface waves that interfere with the bulk wave. This is a problem for the purpose of internal imaging. In the case of ultrasound generated by laser beams or electron beams, the sensitivity of the system is still an issue. Tightly focused ultrasound beams, and laser or electron beam generated ultrasound beams, tend to be best suited to microscopic application, and are not generally applicable to large scale imaging.

Scanning by the known systems is also very slow compared to the capability of electronic systems today. There is a need for significantly increased scanning speeds for test specimens with irregular contact surfaces.

SUMMARY OF THE INVENTION

Accordingly, it is an object of the present invention to achieve a convenient and simple method for coupling a conventional ultrasonic transducer to a test specimen having an irregular contact surface for imaging of interior structures and flaws in the test specimen.

Another object of the present invention is to achieve a generally applicable method, which does not require electronic tuning or adjustments, for coupling a conventional ultrasonic transducer to a test specimen having a contact surface that is not flat, for non-destructive evaluation of structures and flaws in the interior of the test specimen.

A still further object of the present invention is to achieve a method for coupling a conventional ultrasonic transducer to a test specimen having an irregular contact surface and still allowing very rapid scanning of structures and flaws in the interior of the test specimen.

Still another object of the present invention is to provide a simple and generally applicable device for coupling an ultrasonic transducer to a test specimen for the purpose of ultrasonic imaging of the interior of the test specimen.

These and other objects are accomplished by a method for non-destructive evaluation of interior structures and flaws in a test specimen, comprising the steps of providing an ultrasonic transducer with a smooth surface, providing a plurality of ultrasonic wave guides having equal delay times, arranging the wave guides in parallel between the ultrasonic transducer and the surface of the test specimen, coupling one end of each wave guide ultrasonically to the transducer, and coupling the other end of each wave guide ultrasonically to the surface of the test specimen.

A device according to the invention for coupling an ultrasonic transducer to a test specimen comprises a plurality of ultrasonic wave guides having equal delay times for ultrasonic pulses transmitted therethrough, means for arranging the wave guides in parallel between the transducer and the test specimen, means for coupling a first end of each wave guide ultrasonically to the transducer, and means for coupling a second end of each wave guide to the test specimen. A preferred form of such a device has wave guides made from thin bendable wires packed in a brush-like configuration.

BRIEF DESCRIPTION OF THE DRAWING

The present invention and the objects achieved by it will be understood from the description herein, with reference to the accompanying drawings, in which:

FIG. 3 is a lateral view of an ultrasonic brush according to the present invention;

FIG. 4 is a top plan view of the ultrasonic brush shown in FIG. 3;

FIG. 5 is an enlarged cross-sectional view of part of the ultrasonic brush shown in FIG. 3;

FIGS. 6(a) and 6(b) are illustrative views of one wave guide in the ultrasonic brush shown in FIGS. 3–5 before and after application against the surface of a test specimen; and FIGS. 7(a) and 7(b) are illustrative views of one wave guide with its bristle end cut at a sharp angle according to the present invention, before and after application against a test specimen.

DETAILED DESCRIPTION OF A PREFERRED EMBODIMENT

Figure 1:
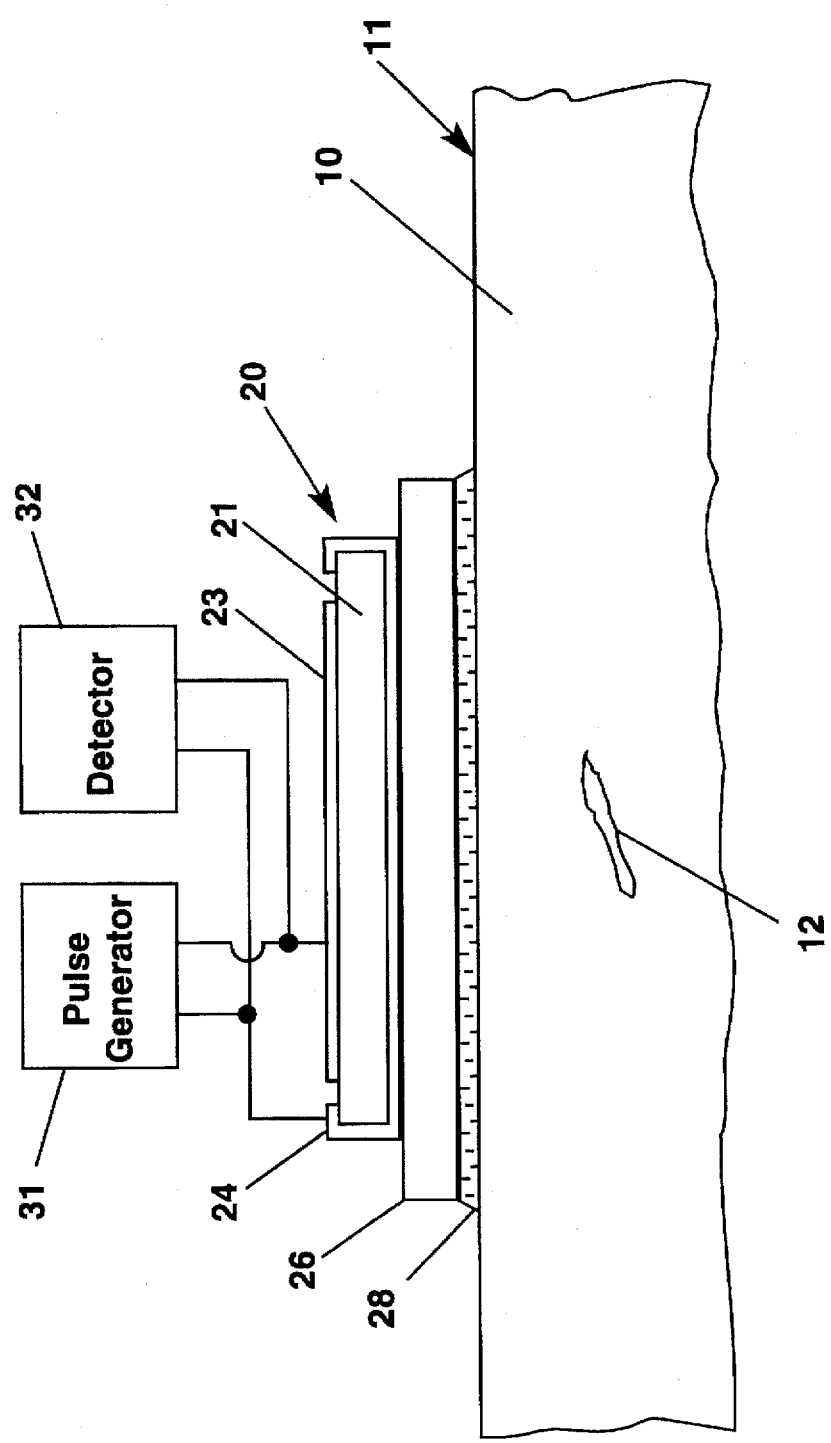
FIG. 1 is a schematic view representing a prior art system for ultrasonic imaging of the interior of a test specimen with a flat contact surface.

A conventional system for non-destructive ultrasonic imaging of interior structures and flaws in a test specimen is illustrated schematically in FIG. 1, which shows a vertical section through a test specimen 10 and associated ultrasonic imaging components.

An ultrasonic transducer 20 is coupled acoustically to a flat surface 11 on a test specimen 10 via a quarter wave coupling plate 26 and a thin layer 28 of liquid or solid contact material. The transducer 20 is made from a thin plate 21 of piezoelectric material with electrodes 23 and 24 deposited on opposite sides. When a short electric pulse of electrical oscillations from a pulse generator 31 is applied between the two electrodes 23, 24, the piezoelectric plate 21 oscillates, and a coherent ultrasonic wave is emitted from the transducer 20. The frequency of the ultrasonic wave typically is in the MHz range. The quarter wave coupling plate 26 and the contact material 28 assures efficient transmission of the coherent ultrasonic wave from the transducer 20 into the surface 11 of the test specimen 10, and a coherent wave travels into the test specimen 10.

When a flaw 12 or the opposite side of the test specimen 10 is encountered by the ultrasonic wave, part of the wave is reflected, and the reflected wave travels back into the transducer 20, which generates an electrical signal corresponding to the reflected wave. This electrical signal is sensed by a detection device 32, which calculates the time elapsed from the moment when the pulse was sent out until the moment when the reflected pulse was detected. The detection device 32 also includes circuits that multiply this time by the known bulk speed of the ultrasound wave in the test specimen for calculating the distance the wave had travelled before the flaw 12 was encountered, and means for displaying the distance from the surface 11 to the flaw 12 on a CRT or a printer.

Figure 2:
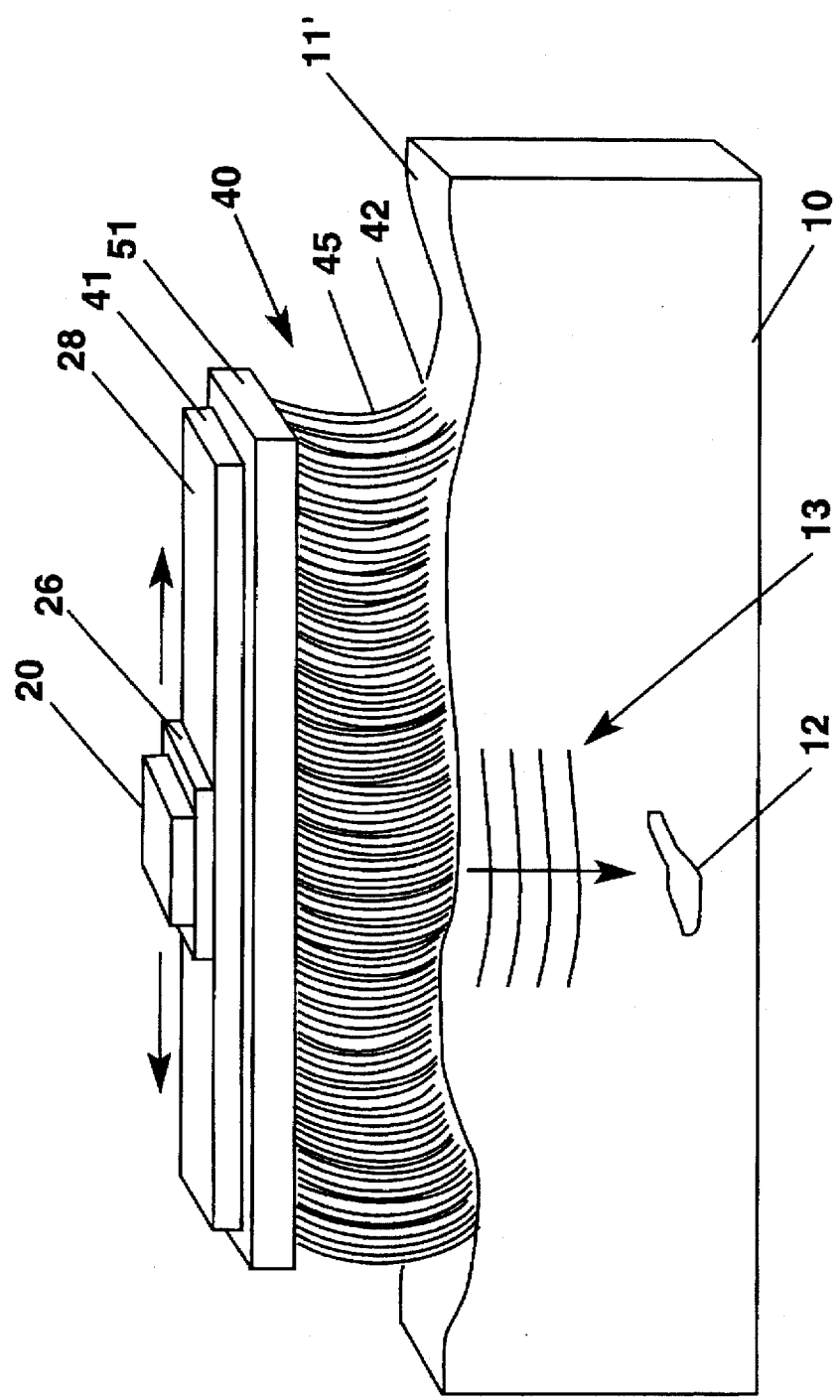
FIG. 2 is a perspective view showing a preferred embodiment of the present invention.

The known system described above is easy to use, and it works well as long as the test specimen 10 has a flat and smooth contact surface 11 for the ultrasonic transducer 20. However, as shown in FIG. 2, if the contact surface 11' is irregular, this system does not work at all, because the irregular surface geometry will cause severe mode conversions, phase distortions and signal reflections. It does not help to fill the voids between the transducer 20 and the irregular surface 11' with a homogenous wet or dry couplant 28, because the couplant 28 causes delays between the transducer 20 and the surface 11' that varies with the thickness of the couplant layer 28.

FIG. 2 is a perspective view of a system employing the present invention, which provides a simple solution to the problem of transmitting a coherent ultrasonic wave from a flat transducer 20 into a test specimen 10 with an irregular contact surface 11'. As shown in FIG. 2, a plurality 40 of thin, bendable wave guides 45 of equal length are arranged in parallel configuration between a flat ultrasonic transducer 10 and the irregular contact surface 11'. One end 41 of each wave guide 45 is coupled to the transducer 20 via a quarter wave plate 26 and a thin layer 28 of acoustic coupling material, and the other end 42 of each wave guide 45 is pressed against the contact surface 11'. A holder or header 51 is used for retaining the plurality 40 of wave guides.

The individual wave guides 45 will bend as indicated in FIG. 2, with those pressing against peaks on the contact surface 11' bending more than those that are pressed against valleys. All of the wave guides 45 will accordingly be in acoustic contact with both the transducer 20 and the contact surface 11' of the test specimen 10, and the ultrasonic wave 13 will travel the full length of all of the wave guides 45 between the transducer 20 and the surface 11'. The wave guides are all equally long, and are made from the same material, so they all have the same time delay for the ultrasonic wave 13. The ultrasonic wave 13 will accordingly reach all parts of the surface 11' simultaneously, and the ultrasonic wave 13 infused into the test specimen 10 will be a coherent wave, as required for ultrasonic imaging, in spite of the irregularity of the contact surface 11'.

When a transmitted wave 13 encounters a flaw 12, the reflected wave is transmitted from the surface 11' via the individual wave guides 45 back to the transducer 20, from which it is detected and displayed as described above. The reflected wave is again transmitted without risk of incoherence, in spite of the irregular contact surface 11', because all of the individual wave guides 45 have the same delay time. The only effect the wave guides 45 have on the detected signal is an added delay equal to twice the delay time of the wave guides 45. This delay is constant, so it can easily be removed by the detector unit 32 before the flaw 12 is displayed.

The display will show the distance between the flaw 12 and the nearest part of the surface 11', which is not flat, so the displayed picture will be a distorted representation of the flaw 12. This is not a detriment in most applications, and the distortion can be eliminated by feeding a scan of the surface 11' to memory circuits in the detector 32 for correction of the displayed picture if an undistorted picture of the flaw 12 is required.

FIG. 5 is an enlarged cross-sectional view of a tight bundle 40 of wave guides 45. Each wave guide 45 consists of a length of thin wire 46 with diameter D1 made from metal, doped fused silica, or non-metal material. The diameter D1 of the wire must be much less than the wavelength of the ultrasonic wave in the wire. The wavelength of a 1 MHz wave will vary between about 2 mm and about 8 mm depending on the material used in the wire, so the actual wire diameter D1 will be in the order of 0.1 mm or smaller. The contact area between a wave guide 45 and the surface 11' will thus always be point-like. By varying the wire material in the wave guides 45, a wide range of acoustic impedances for the wave guide 45 can be obtained. When the acoustic impedance of the test specimen material is known, it will accordingly be possible to select a wave guide with a compatible acoustic impedance, which ensures efficient acoustic coupling between the wave guides 45 and the test specimen 10.

A thin coating or cladding 47 is usually added to the wire 46 to improve the transmission of ultrasound lengthwise through the wave guide 45 while reducing lateral leakage. Such coating also reduces the risk of out-of-phase signals being transmitted between wave guides 45 in lateral contact with each other in a bundle 40. The diameter D2 of the coated wave guide 45 determines how close the wave guides 45 can be bundled. The art of manufacturing thin, bendable ultrasonic wave guides with or without cladding is today well known, and such wave guides made to specification are readily available.

A preferred arrangement of the plurality 40 of parallel wave guides 45 is shown in FIGS. 3 and 4, which are a side view and a top view, respectively, of an "ultrasonic brush" according to the present invention. The individual wave guides 45 are arranged as a closely packed bundle 40 with the holder 51 at one end. All ends 41 of the wave guides 45 adjacent the holder 51 are aligned in a contact plane 55 flush with the top surface 52 of the holder 51. The other ends 42 of the wave guides 45 form bristles, which readily will provide acoustic coupling with both even and irregular contact surfaces 11, 11' when the ultrasonic brush 50 is pressed as a unit against a test specimen 10. Care must be taken to make shape and geometry of the components for holder 51 uniform with respect to the wave length in the wave guide, so any sound coupling from one bristle 45 to another via the holding components 51 is avoided. Such parasitic coupling could introduce small differential phase shifts into the wave guides and thus destroy the coherence of the ultrasonic beam at the bristle end 42 of the wave guides 45.

The flat contact plane 55 of the ultrasonic brush 50 provides a suitable contact surface for a standard ultrasonic transducer 20. The transducer 20 can act on this contact plane 55 directly, or via a thin coupling layer 28 and a quarter wave plate 26, which provide improved transmission efficiency.

Lateral scanning of the plane 11' can be made with high speed if the ultrasonic brush has a contact plane 55 that is substantially longer than the surface of the transducer 20, as shown in FIGS. 3 and 4, so the transducer 20 can scan along the contact plane 55, as shown by arrows, while the ultrasonic brush 50 remains stationary.

Scanning in a transverse direction (up and down in FIG. 4) can be made by moving the brush 50 back and forth with the transducer 20 stationary on the contact plane 55. The ultrasonic brush 50 can also be made with a contact plane 55 that is wider than the transducer 20, so the transducer 20 can scan crosswise on the contact plane 55 while the ultrasonic brush 50 remains stationary.

The ultrasonic brush 50 can also be made with a top contact plane 55 matching the transducer 20, in which case scanning is made by moving the brush 50 and the transducer 20 as a unit along the surface 11' of the test specimen 10. An array of ultrasonic brushes 50 with transducers 20 attached can also be distributed over the surface 11' for real-time imaging of a large part of the interior of the test specimen 10.

In the above description of the present invention, it has been assumed that the bristle ends 42 of the wave guides 45 are cut at right angle to the wave guide axis. The contact between the wave guide 45 and the surface 11' of the test specimen 10 in this case is illustrated in FIGS. 6(a) and 6(b), which show an enlarged end 42 of a wave guide 45 before it contacts the surface 11' and after the bristles 45 of the ultrasonic brush 50 have been pressed against the surface 11', respectively. This design of the bristle ends 42 of the wave guides 45 will deliver longitudinal bulk waves or shear waves into the test specimen 10, depending on the mode generated by the transducer 20.

The invention also provides a new method for transmitting a shear wave into a test specimen 10 via parallel wave guides 45 with equal delay times, without the need for a shear mode transducer 20. This part of the invention is achieved by cutting the bristle ends 42' of the wave guides 45 at a specific angle of less than 90° with the axis, as shown in FIG. 7(a). Such bevelled bristle ends 42' will contact the surface 11' of the test specimen 10 as shown in FIG. 7(b). Longitudinal waves transmitted from a longitudinal mode transducer 20 along the wave guide 45 will reach different parts of the surface of the bevelled end 42' at different moments, and thereby produce a differential phase effect in the surface 11', which will restrict the generation of longitudinal bulk waves while enhancing a shear drive at the surface 11' of the test specimen. By choosing a suitable angle for the bevel 42' of the bristle ends, pure shear mode waves can be infused into the test specimen 10.

It should be understood from the description above that the invention requires wave guides with equal delay times, but that it does not matter how this is achieved. The wave guides 45 described in connection with the preferred form of the invention are stated to be equally long and made of the same material, which is the preferred design. It is possible, however, to make the wave guides 45 with differing lengths, if at the same time different materials with different wave velocities are used, so the delay time for all the wave guides 45 are kept constant.

Numerous modifications and adaptations of the present invention will be apparent to those skilled in the art. Thus, the following claims are intended to cover all such modifications and adaptations which fall within the true spirit and scope of the present invention.

What is claimed is:

1. A method for non-destructive evaluation of interior structures and flaws in a test specimen, comprising the steps of:
   (a) providing an ultrasonic transducer with a smooth surface;
   (b) providing a plurality of flexible ultrasonic wave guides having equal delay times;
   (c) arranging said wave guides in parallel between said ultrasonic transducer and a surface of the test specimen;
   (d) coupling one end of each of said wave guides ultrasonically to said ultrasonic transducer; and
   (e) coupling the other end of each of said wave guides ultrasonically to said surface of the test specimen, the end coupled to said surface of the test specimen being free to engage said surface of the test specimen regardless of test specimen geometry.

2. A method for non-destructive evaluation of interior structures and flaws in a test specimen according to claim 1, wherein said wave guides are made of thin and bendable wires.

3. A method for non-destructive evaluation of interior structures and flaws in a test specimen according to claim 2, wherein said wave guides have a diameter smaller than the shortest wavelength of a chosen range of frequencies of ultrasound in a material from which the wave guides are made, and wherein each of said wave guides has a coating for improving the sound confinement in said wave guides.

4. A method for non-destructive evaluation of interior structures and flaws in a test specimen according to claim 3, further comprising the steps of:
   (f) arranging said wave guides in a bundle;
   (g) providing a header at one end of said bundle for assembling said wave guides in parallel, wherein said wave guides form bristles of an ultrasonic brush, each of said bristles having a header end and a bristle end;
   (h) arranging said header end of each of said bristles to form a substantially smooth surface conforming to said transducer; and (i) pressing said bristle end of each of said bristles against said surface of the test specimen, wherein each of said bristles bends to automatically conform to said surface of said test specimen.

5. A method for non-destructive evaluation of interior structures and flaws in a test specimen according to claim 4, further comprising the step of:

(j) cutting the bristle end of said wave guides at an angle less than 90°.

6. A method for non-destructive evaluation of interior structures and flaws in a test specimen according to claim 4, wherein said header has a larger area than said ultrasonic transducer, wherein said ultrasonic transducer can be moved along said header for rapid scanning of said test specimen.

7. A device for coupling an ultrasonic transducer having a predetermined coupling area to a test specimen, comprising:

(a) a plurality of flexible wave guides having equal delay times for ultrasonic pulses transmitted therethrough;

(b) means for arranging said wave guides in parallel between said transducer and said test specimen;

(c) means for coupling a first end of each of said wave guides acoustically to said transducer; and (d) means for coupling a second end of each of said wave guides acoustically to said test specimen wherein said second end is free to engage said test specimen regardless of test specimen geometry.

8. A device for coupling an ultrasonic transducer to a test specimen according to claim 7, wherein said wave guides are thin and bendable wires.

9. A device for coupling an ultrasonic transducer having a predetermined coupling area to a test specimen according to claim 8, wherein said wave guides have a diameter smaller than the shortest wavelength of a chosen range of frequencies of ultrasound in a material from which the wave guides are made, and wherein each of said wave guides has a coating for improving the sound confinement in said wave guides.

10. A device for coupling an ultrasonic transducer to a test specimen according to claim 9 wherein said wave guides form a brush-like arrangement and wherein said means for coupling a first end comprises a brush head and each of said second end of said wave guides forms a bristle.

11. A device for coupling an ultrasonic transducer to a test specimen according to claim 10, wherein said brush head has an area larger than the coupling area of said transducer.

12. A device for coupling an ultrasonic transducer to a test specimen according to claim 7, wherein each said second end said wave guides is cut at an angle less than 90°.

* * * * *